United States Patent [19]

Karlstam

[11] Patent Number: 4,904,594

[45] Date of Patent: Feb. 27, 1990

[54] ENZYME PREPARATION CAPABLE OF DEGRADING GLYCOSAMINO-GLYCAN, AND A METHOD FOR PRODUCING SAID PREPARATION

[75] Inventor: Björn O. E. Karlstam, Björklinge, Sweden

[73] Assignee: Pharmacia AB, Uppsala, Sweden

[21] Appl. No.: 65,591

[22] Filed: Jun. 23, 1987

[30] Foreign Application Priority Data

Jul. 9, 1986 [SE] Sweden .................................. 8603051

[51] Int. Cl.[4] .............................................. C12N 9/26
[52] U.S. Cl. ..................................... 435/201; 435/947
[58] Field of Search ................................ 435/201, 947

[56] References Cited

U.S. PATENT DOCUMENTS 4,695,457 9/1987 Hellgren et al. .................. 424/94.63

OTHER PUBLICATIONS

Kitamikado, M. et al, Nippon Suisan Gakkaishi Bull, Jap. Soc. Sci. Fish., 35 (1969), pp. 466–470.
Yomamoto, H. et al, Nippon Susian Gakkaishi Bull, Jap. Soc. Sci. Fish., 37 (1971), pp. 621–670.
Galas, E. et al, Chemical Abstracts, 98 (1983), 13 723 m, Pol PL 115, 567.
Kimoto, K. et al, Agric. Biol. Chem., 48 (1984), pp. 1819–1823.
Chen, C-S. et al, J. Food Biochem, 2 (1978), pp. 349–366.
Experientia, 43 (1987), p. 578, Campbell et al.

Primary Examiner—Robert A. Wax
Attorney, Agent, or Firm—Fred Philpitt

[57] ABSTRACT

Glycosaminoglycan-degrading enzyme preparation containing krill hyaluronidase, and a method of producing said preparation.

2 Claims, No Drawings

ENZYME PREPARATION CAPABLE OF DEGRADING GLYCOSAMINO-GLYCAN, AND A METHOD FOR PRODUCING SAID PREPARATION

The invention is concerned with a group of glycosamino-glycan-degrading enzymes which have not been known heretofore and are to be found in aquatic crustaceans belonging to the order of Euphausiaceae, especially those of the genus Euphausia such as the species *Euphausia superba* (Antarctic krill). The enzymes contemplated in the context of this invention are capable of degrading hyaluronic acid and will therefore henceforth be referred to as "hyaluronidases". The designation "krill" is commonly used to apply to all the crustaceans of the aforesaid order.

*Euphausia superba* is the krill species most commonly occurring in the oceanic regions surrounding Antarctica. Krill upon dying will autolyse very quickly due to their very potent digestive enzymes. A plurality of reports have been issued concerning krill proteases which have been suggested for use as inter alia cleaning-purpose enzymes (6). In view of the fact that krill will feed primarily on phytoplankton which contains large amounts of various carbohydrates (in addition to protein) it had been assumed that krill might also contain active polysaccharide-degrading enzymes (3, 13); it may be noted in this context that Chen et al (3) have demonstrated the presence of chitinase activity in crude krill extract. However, there has been no hint that this activity might be caused by a specific enzyme that exhibits hyaluronidase activity.

Glycosaminoglycans (=GAG:s) are also called "mucopoly-saccharides" and are characterized in that they are polysaccharides containing aminated monosaccharide units which may be present in an amidated form. The GAG:s moreover may contain e.g. sulfated monosaccharide and uronic acid structures such as glucopyranosyluronic and idopyranosyluronic units. Examples of GAG:s are: chitin, chondroitin, chondroitin sulfates A, B and C, heparan sulfate, heparin, hyaluronic acid and keratan sulfate.

In the context of the present invention, hyaluronic acid is the most important one of the glycoaminoglycans. It consists of repeating units of the disaccharide (1→4) O-beta-D-glucopyranosyluronic acid (1→3) 2-acetamido-2-deoxy-beta-D-glucopyranose.

Hyaluronidase is by definition an enzyme capable of degrading the hyaluronic acid into smaller fragments, in the first place tetrasaccharides although also simple mono- or di-saccharide units may be formed. It is most desirable that the term "hyaluronidase" be used for enzymes preferentially utilizing hyaluronic acid, even though the said term is occasionally used for other hyaluronic acid-cleaving enzymes preferring other GAG:s. Thus, a hyaluronidase is an enzyme that has to be capable of cleaving one of the hyaluronic acid glycoside linkages and must therefore be either a glucuronidase (like for instance beta-(1,3)-glucuronidase releasing glucuronisyl groups) or a hexosaminidase (such as beta-(1,4)-glucosaminidase releasing amidated glucosaminyl groups). Glucuronidases and hexosaminidases may be of the endo or exo type. It is known that hyaluronidase may act in substantially one of the following two ways: Either by way of a hydrolytic cleavage (hydrolase, for example testicular hyaluronidase) or by way of a cleavage proceeding in the form of an elimination reaction (eliminase, for example bacterial hyaluronidase from Streptomyces).

For a general survey of hyaluronidases see Meyer, K et al. (9).

In an International Type Search Report prepared by the Swedish Patent Office in connection with the prosecution of the priority application, references 15–19 have been cited. None of them discloses krill hyaluronidases.

Hyaluronidase has been put to use in many fields of practical application and is commercially available from a plurality of producers. A feature common to these various fields of application is that they are all directed to modifying reaction processes of hyaluronic acid in any given, hyaluronic acid-containing system either in vivo or in vitro. The in vivo use of the enzyme has been suggggested in connection with various therapeutic treatments. For instance it has been proposed that the enzyme should be employed together with drugs, the function of the hyaluronidase then being to enhance the spreading of the drug through a tissue (note that hyaluronidase is also called "spreading factor"). In therapeutic contexts the enzyme moreover is considered to have positive effects 1) on myocardial infarctions (5), 2) on retinal function (14), and 3) in combination with cytostatics in the treatment of cancer tumors (1). In vitro, the enzyme has been employed for depolymerizing hyaluronic acid en e.g. a cell-free system, or for stimulating hyaluronic acid synthetase in e.g. cell culturing procedures (11).

Hyaluroonidases have been obtained mainly from bovine testicles, bacteria and leeches. These materials had relatively low contents of hyaluronidase, thus involving high prices for hyaluronidase preparations possessing an acceptable degree of purity for in vivo use. Consequently there is a demand for hyaluronidase preparations which are both cheap and better.

The hyaluronidase preparations of this invention are characterized by containing that hyaluronidase which is to be found in the crustaceans mentioned in the beginning of this specification. Sources in addition to krill from which krill hyaluronidase can be isolated are potentially also culturing media for cells that have been caused to produce the enzyme by means of recombinant techniques. Our studies up to now concerning krill hyaluronidases have shown that these enzymes may have a molecular weight of $8 \times 10^4$, such as $80\,000 + 3\,000$ daltons, a pH optimum of 4,5–6,0, and a pI (isoelectric point) within the pH range of 4–7, with a possibility that there may be coexisting isoenzymes. The hyaluronidases may be glycoproteins having a Con A-binding capacity (that is, having terminal monosaccharide residues of an alpha-D-mannopyranoside or alpha-D-glycopyranoside structure). The enzyme activity detected up to now appears to indicate that krill hyaluronidase has endoglucuronidase-like activity, i.e. is an endoglucuronidase. It is not entirely impossible that krill hyaluronidases in future studies will be found to possess also other specificities enabling them to efficiently degrade hyaluronic acid.

The hyaluronidase preparations of the invention exhibit a hyaluronidase activity exceeding 2,0 U/mg of protein from the source of raw material (that is in most cases krill protein), e.g. exceeding 10 U/mg of protein from said source, for instance exceeding 20, 50 or 100 U/mg of protein from said source. It is possible to produce preparations having activities exceeding 250 U/mg of protein from said source of raw material. The aforesaid activities are to be measured according to the method set forth in the below exemplification.

Hyaluronidases of the invention can be prepared by extracting fresh krill or fresh-frozen krill which has been homogenized. This extraction should be performed with an aqueous medium, e.g. water. It is then possible to isolate the enzyme from the resultant extract by means of separating methods based on the aforesaid properties of krill hyaluronidases. Methods that may be employed are chromatographic methods like affinity, gel and ion exchange chromatography, HPLC, FPLC, chromatofocusing etc., or preparative elecrophoresis. Moreover also dialysis, ultrafiltration and membrane filtration are potentially useful methods. The extraction and honogenization mentioned above are preferably carried out in the cold, below or close to $+4°$ C. It is also advantageous to remove lipids from the resultant aqueous extract (crude extract) by extracting it with a lipid-dissolving solvent before it is subjected to further purification. Additional details of krill hyaluronidase isolation will be apparent from the below exemplification.

Krill hyaluronidases of the invention may potentially be employed in ways that are usual for hyaluronidases; see above.

In a preparation according to the invention isolated krill hyaluronidases may be present as a powder (e.g. freeze- or spray-dried). The hyaluronidase may also be present in admixture with, dissolved in or in some other manner incorporated in various vehicles which are suitable for the purpose contemplated - for example water (e.g. physiological saline). etc.

The invention is set forth in the attached claims which form an integral part of this specification.

The invention will now be illustrated by means of the scientific work that has formed the actual basis of this invention. The exemplification is not meant to limit the invention in any respect; on the contrary it should be understood that a multitude of variations are feasible within the scope of the present invention.

Experimentals

Materials

Bovine testicular hyaluronidase, 5-sulfosalicylic acid (S-2130), phenolphthalein glucuronic acid (P-0376), laminarin (L-9634), methyl alpha-D-mannopyranoside (M-6882) were from SIGMA (USA). Hyaluronic acid (Healon®) was from Pharmacia AB (Sweden). Ultrafiltration cell and membranes (YM 10) were from Amico Corp. (USA). Tris-hydroxymethylaminomethane (TRIS), 3,5-dinitrosalicylic acid, potassium-sodium tartrate ($C_4H_4O_6KNa \times 4H_2O$), cetyl pyridinium chloride monohydrate were from Merck (U.S.A.). Con A Sepharose®, Superose® 6 prep grade, Agarose A, polyacrylamide gradient gels (PAA 4/30), gel filtration kit, isoelectric focusing calibration kit (pH 3–10) and Pharmalyte® (pH 3–10) were from Pharmacia AB (Sweden). The chromatographic and electrophoretic equipment obtained from Pharmacia AB were K 16/20 and K 16/100 columns, single path monitor (UV-1), electrophoresis power supply (EPS 500/400), gel electrophoresis apparatus (GE-4), electro-phoresis constant power supply (ECPS 3 000/150), volthour integrator (VH-1), destainer power supply (DPS), gel destainer apparatus (GD-4), Superose® HR 10/30 column and Mono Q HR 5/5 anion exchange column connected to an FPLC system.

Methods

A. Preparing crude krill extract

Krill (Euphausia superba) caught during the Antarctic summer and immediately frozen and then stored at about $-20°$ to $-40°$ C. is placed in a $+4°$ C. environment. When almost thawed 100 g thereof are mixed with 200 ml of deionized water. The mixture is homogenized and then centrifuged until the homogenate is clear. The upper phase (=the extract) is decanted and filtered, the filtrate then being treated with three times its volume of a lipid-dissolving solvent. After phase separation the aqueous phase is recovered and used as according to B below. This work was carried out in a cold room at about $+4°$ C.

B. Affinity chromatography on Con A Sepharose®

Commercially available Con A Sepharose® was washed with buffer (20 mM TRIS-HCl, pH 7,5, 1 mM $Mn^{2+}$, 1 mM $Mg^{2+}$, 1 mM $Ca^{2+}$, 1M NaCl) and packed into a K 16/20 column to a height of 15,5 cm corresponding to a bed volume of about 31 ml. The column was then equilibrated with the aforesaid buffer at room temperature. 15–30 ml of crude extract from A having the same salt concentration as the buffer were applied to the column and eluted with 200 ml of the above buffer (about 6 bed volumes) at a flow rate of 13 ml/h. This was followed by desorption with the aid of buffer containing 5 % (w/v) of methyl alpha-D-mannopyranoside. The elution was continuously monitored at 280 nm until no UV-adsorbing material was demonstrable in the eluent. The fractions that had been collected (2 ml/fraction) were assayed for hyaluronidase activity. The active fractions were pooled and concentrated by means of an Amicon filter (YM 10).

C. Gel Filtration

About 4 ml (about 2 % of the bed volume) of the concentrate obtained from B was applied to a Superose® 6 prep grade column K 16/100 (1,6 cm x 100 cm) in a cold room at $+4°$ C., said column having been equilibrated with 50 mM TRIS-HCl buffer (pH 7,5). The column was eluted with the same buffer at a flow rate of 12 ml/h. Elution was monitored spectrophotometrically at 280 nm. The fractions obtained (2 ml/fraction) were assayed for hyaluronidase activity, and fractions showing activity were pooled.

D. FPLC

The pooled fractions from step C were purified further on a strong anion exchange column (Mono Q HR 5/5) equilibrated at room temperature with the same buffer as in step C. Of the pooled fractions from step C, 4 ml was applied to the column, the proteins being then eluted with a stepwise gradient of NaCl from 0 to 0,18 M, 0,18 to 0,34 M, 0,34 to 1,0 M. The fractions (1 ml/fraction) were assayed for hyaluronidase, beta-glucuronidase and endo (1,3)-beta-D-glucanase activities. The active fractions corresponding to each respective enzyme were separately pooled.

E. Assay of Hyaluronidase Activity

A simple plaque method according to Richman et al. (12) was used for hyaluronidase activity determination comprising, in brief terms, the following: Hyaluronic acid (Healon®) was incorporated in a 1,5 % (w/v) agarose gel. From wells that had been punched into the gel the enzyme was allowed to diffuse into the gel for 20 hours at $37°$ C. The undigested hyaluronic acid was then precipitated by addition of cetyl pyridinium chloride, resulting after about 30 minutes in the formation of clear circles around each respective well. The diameters of the circles were proportional to the logarithm of the concentration of enzyme solution added to each respective well. Testicular hyaluronidase was used as a reference for obtaining a standard curve. Assays were made with the pooled fractions from the respective steps A—D above.

F. Assay of Beta-Glucuronidase

This activity was assayed in accordance with a method described by Fishman et al (4). A series of tubes was filled with 0,8 ml of 0,1 M NaAc, pH 4,5, +0,1 ml of phenolphtalein mono-beta-glucuronic acid, pH 7,6, and was incubated for 5 minutes at 37 °C. At timed intervals 0,1 ml of enzyme solution from step D above was added to each of the tubes, whereas the blank received 0,1 ml of distilled water. The tubes were incubated for 30 minutes at 37 °C. The enzymatic reaction was stopped by addition of 5,0 ml of 0,2 M glycine, 0,2 M NaOH, whereupon the tubes were cooled and UV adsorption was read at room temperature at 540 nm. The number of μmoles of phenolphthalein liberated was calculated with the aid of a standard curve. One unit (U) of enzyme will cleave one μmole of phenolphthalein mono-beta-glucuronic acid per minute at 37° C. and pH 4,5.

G. Assay of Endo (1,3)-Beta-D- Glucanase

This enzyme activity was assayed in accordance with a method described by Turkiewicz et al (13). The substrate employed was laminarin which consists of beta-D-glucose residues mainly connected via 1,3 linkages. The enzyme activity is expressed as μmoles of glucose released per minute. The released glucose was measured with 3,5-dinitrosalicylic acid as described by Bernfeld (2). 0,5 ml of enzyme solution from step D above, buffered with Na phosphate (10 mM pH 6,2), was incubated with 0,5 ml of substrate solution (1 mg of laminarin/ml in the phosphate buffer) for 10 minutes at 50 °C. Immediately thereafter 1,0 ml of 3,5-dinitrosalicylic acid reagent was added, and the tubes were inserted in a boiling water bath for thus being heated for 5 minutes. Finally, the samples were cooled and 8,0 ml of distilled water was added. The absorbance was read immediately at 540 nm. The number of μmoles of liberated glucose was calculated from a standard curve, and enzyme activity was expressed as units (μmoles/unit time).

H. Protein determination

The protein concentrations in the different enzyme preparations were determined by the method of Lowry et al (8) using BSA as as reference protein.

I. POLYACRYLAMIDE GRADIENT GEL ELECTROPHORESIS (g-PAGE)

The electrophoretic buffer was 40 mM TRIS-HCl, 20 mM NaAc, 2 mM EDTA, pH 8,4. The sample composition was: 56 μ of concentrated protein, 15 μ of 50 % (w/v) sucrose and 5 μ of 0,1 % (w/v) bromophenol blue. 15–30 μ of the sample formulation (40 μg of protein) was applied to pre-equilibrated gel (70 V for 1 hour). Electrophoretic conditions were 150 V (35 mA/gel) for 20 minutes ("run in") and thereafter 100 V (25 mA/gel) for about 5 hours. The proteins were fixed by means of electrophoresis at 24 V for 30 min. in a solution of isopropanol and acetic acid (25 % and 10 % respectively, v/v). The gels were stained with 0,2 % (w/v) of Coomassie brilliant blue in a solution of methanol and acetic acid (25 % and 10 % respectively, v/v) for 2 hours. Destaining was carried out during 45 minutes in the same solution but without any dye therein.

J. Isoelectric Focusing (IEF)

Casting of gels and focusing conditions were performed as according to the producer's instructions (10). A polyacrylamide gel of 1 mm thickness was cast (5 % w/v total acrylamide and 3 % cross-linking agent) containing Pharmalyte®, pH 3–10. The electrode solutions consisted of 0,1 M sulfuric acid (anode) and 1 M NaOH (cathode). Prior to sample application the gel was pre-focused for 500 Vh at a constant power of 30 W. 20 μl of concentrated and desalted final pool from step D containing 50 μg of protein was applied to the gel. Focusing was allowed to proceed for 5 000 Vh (3,5 h) at a constant power of 30 W ($V_{max}$=2 500 V). After focusing, the proteins were fixed and Pharmalyte® was removed with 5 % (w/v) 5-sulfosalicylic acid and 10 % (w/v) trichloroacetic acid for 60 minutes. The gel was then washed for 30 min. with a destaining solution consisting of 30 % (v/v) methanol and 10 % (v/v) acetic acid. Staining of the protein was performed with 0,2 % (w/v) Coomassie brilliant blue dissolved in the destaining solution. Destaining was carried out with many changes of wash solutions.

K. Hyaluronidase Activity Measured By Zymogram

A substrate gel was cast by means of mixing 2 ml of Healon® (10 mg/ml), 3 ml of Na citrate buffer (pH 5,3, 0,15 M NaCl, 0,02 % NaN$_3$) and 5 ml of 2 % agarose A. The mixture was heated with stirring for about 2 minutes, whereupon it was poured upon an 8×8 cm$^2$ Gel Bond film. G-PAGE was performed as above. Immediately after termination of the electrophoresis procedure the gel was incubated for 15 minutes with the citrate buffer. Face to face the electrophoretic gel and the substrate gel were then placed onto a glass plate. The resultant three-layer "sandwich" was placed in a humidity chamber and left there for 24 hours at 37° C. Undigested hyaluronic acid was then precipitated with cetyl pyridinium chloride.

For IEF, the substrate solution was poured directly on the IEF gel after electrofocusing. The plate was introduced into a humidity chamber and left there for 24 hours at 37 °C. Undigested hyaluronic acid was precipitated as stated above.

L. Molecular Weight Determination

Molecular weights were determined by means of gel filtration on a Superose® 12 HR 10/30 column connected to an EPLC system. The column was equilibrated with 50 mM TRIS-HCl, pH 7,5, containing 0,15 M NaCl; ferritin (440 000), aldolase (158 000), BSA (67 000), ovalbumin (43 000) and chymotrypsin (25 000) were used as reference proteins. The elution volumes plotted against log $M_w$ gave a straight line.

M. Determinatoin of pH Optimum

The hyaluronidase activity was determined in various substrate gels (see E) in which the pH had been adjusted to different values with the aid of an 0,05 M citratephosphate solution.

Results and Discussion

In step B hyaluronidase was purified by means of affinity chromatography on Con A Sepharose®. This adsorbent is known to interact specifically with glycoproteins having terminal alpha-D-glucopyranoside or alpha-D-mannopyranoside residues. The fact that hyaluronidase, beta-glucuronidase and endo(1,3)-beta-D-glucanase have bound strongly to the column suggests that these enzymes possess some of said terminal sugar residues. The bound proteins were desorbed from the column with 5 % methyl alpha-D-mannopyranside.

In step C the three enzymes were eluted together; an efficient purification from other proteins took place in this step.

In step D the three enzyme activities could be separated from one another by means of ion exchange chromatography on Mono Q. Three protein peaks were obtained which were designated I, II and III (I being eluted first and III last). The fractions within each peak were analyzed as set forth above in respect of their hyaluronidase, beta-glucuroidase, and endo (1,3)-beta-D-glucanase activities. Peak III contained a high hyaluronidase activity which could notbe demonstrated in peaks I and II. The beta-glucuroidase activity was associated with peak I, while the endo(1,3)-beta-D-glucanase activity was to be found in peak II and, to some extent, in peak III.

The isolate hyaluronidase was then studied further with respect to purity, isoelectric point, pH optima and molecular weight.

When g-PAGE was carried out, peak III showed a major protein slightly contaminated with a minor number of other components. A hyaluronic acid zymogram on the separation gel showed that the major band was associated with the hyaluronidase activity.

The isoelectric focusing pattern in combination with a hyaluronic acid zymogram demonstrated a high enzyme activity within the pH range of 4 to 7. The activity was associated with several bands, a phenomenon that may be indicative of the presence of isoenzymes.

The pH optimum for hyaluronidase activity was determined to be within the pH range of 4,5 to 6.

TABLE 1

| | Determination of pH optimum | |
|---|---|---|
| pH | circle diameter, mm | |
| 3,0 | 0 | |
| 3,7 | 5 | |
| 4,3 | 8,0 | |
| 4,7 | 9,0 | |
| 5,3 | 9,0 | pH optimum |
| 6,0 | 9,0 | |
| 7,0 | 7,0 | |

The hyaluronidase molecular weight was found to be 80 000 daltons (±3 000 daltons).

The molecular weights of beta-glucuronidase and endo(1,3)-beta-D-glucanase were determined to be 70 000 and 80 000 daltons respectively.

Hyaluronidase specific activity and yields were monitored during the individual purification steps.

TABLE 2

| | Purification of hyaluronidase | | | | | |
|---|---|---|---|---|---|---|
| | Protein | | Hyaluronidase activity | | | Degree of purification |
| Step | mg/ml | total mg | U/mg | total units | % | |
| Crude extract | 45 | 1 350 | 3,4 | 4 650 | 100 | 1 |
| Con A- chromatography | 10 | 48 | 25 | 1 230 | 26 | 7,5 |
| Superose ® 6 gel filtration | 1,1 | 14 | 102 | 1 446 | 31 | 30 |
| FPLC MONO Q ion exchanger | 0,22 | 3,7 | 295 | 1 085 | 23 | 87 |

Endohexosaminidase activity measurements according to Linker (7) could not detect any amounts of liberated N-acetyl glucosamine, thus indicating that the hyaluronidase studied by us might be an endoglucuronidase.

LIST OF REFERENCES

1. Baumgartner, G. et al., J. Exp. Clin. Cancer Res. 4, (1985) p 3.
2. Bernfeld, P., Methods in Enzymol. vol 1 (1955) p 149–158.
3. Chen, C-S. et al., J. Food Biochem. 5 (1981) p 63–68.
4. Fishman, W. et al., J. Biol. Chem. 173 (1948) p 339–56.
5. Flint, E.J. et al., Lancet, April 17 (1982), p 871–74.
6. Hellgren, L., Mohr, V. och Vincent, J., EP-A-107,634.
7. Linker, A., Bergmeyer, Methods of enzymatic analysis, third edition vol IV, enzymes 2, p 257–261.
8. Lowry, O.H. et al., J. Biol. Chem. 193 (1951) p 265–275.
9. Meyer, et al., The Enzymes (1960) p 447–460.
10. Pharmacia Fine Chemicals, Isoelectric focusing, principles and methods.
11. Philipson, L.H. et al., Biochemistry 24 (1985) p 7899–7906.
12. Fichman, P.G. et al., Anal. Biochem. 109 (1980) p 376–381.
13. Turkiewics, M. et al., Polar Biol. 4 (1985) p 203–211.
14. Winkler, B.S. et al., Arch. Opthalmol. 103 (1985) p 1743–46.
15. Kitamikado, M. et al., Nippon Suisan Gakkaishi, Bull. Jap. Soc. Sci. Fish. 35 (1969) p 466–70.
16. Yamamoto, H. et al., Nippon Suisan Gakkaishi, Bull. Jap. Soc. Sci. Fish. 37 (1971) p 621–70.
17. Galas, E. et al., Chemical Abstracts 98 (1983) 13 723 m Pol PL 115,567.
18. Kimoto, K. et al., Agric. Biol. Chem. 48 (1984) p 1819–23.
19. Chen, C-S. et al., J. Food Biochem. 2 (1978) p 349–66.

I claim:

1. A glycosaminoglycan-degrading enzyme preparation, characterized by containg krill hyaluronidase isolated from organisms containing such hyaluronidases.
2. A glycosaminoglycan-degrading enzyme preparation according to claim 1, characterized by having a hyaluronidase activity exceeding 10 U per mg of protein from the source of raw material.

* * * * *